US00PP31749P2

(12) United States Plant Patent
DeVries

(10) Patent No.: US PP31,749 P2
(45) Date of Patent: May 12, 2020

(54) ***ILEX* PLANT NAMED 'B-43-4'**

(50) Latin Name: *Ilex verticillata*
Varietal Denomination: B-43-4

(71) Applicant: Leendert DeVries, Arcata, CA (US)

(72) Inventor: Leendert DeVries, Arcata, CA (US)

(73) Assignee: Humboldt Land Company LLC, Arcata, CA (US)

( * ) Notice: Subject to any disclaimer, the term of this patent is extended or adjusted under 35 U.S.C. 154(b) by 0 days.

(21) Appl. No.: 16/501,774

(22) Filed: Jun. 5, 2019

(51) Int. Cl.
*A01H 5/00* (2018.01)

(52) U.S. Cl.
USPC ..... Plt./247

(58) Field of Classification Search
USPC ..... Plt./247
CPC ..... A01H 5/00
See application file for complete search history.

*Primary Examiner* — Annette H Para
(74) *Attorney, Agent, or Firm* — Samuel R. McCoy, Jr.

(57) ABSTRACT

A new and distinct *Ilex verticillata* cultivar named 'B-43-4' which is characterized by a tall plant height and a large amount of strong, upright main stems with numerous lateral branches, with each bearing very large salmon-orange berries along their entire length. The claimed plant propagates successfully by softwood stem cuttings and has proven to be uniform and stable in the resulting generations.

2 Drawing Sheets

Latin name of the genus and species: The Latin name of the genus and species of the novel variety disclosed herein is *Ilex verticillata.*

Variety denomination:

The inventive variety of *Ilex verticillata* disclosed herein has been given the variety denomination 'B-43-4'.

BACKGROUND OF THE INVENTION

The present invention relates to a new and distinct variety of *Ilex verticillata*, which has been given the denomination, 'B-43-4'. *Ilex verticillata*, known commonly as winterberry, is a deciduous perennial that is widely cultivated for its ornate berries born along the lateral branches. The berries persist for many months through fall and winter, making it an ideal plant for ornamental landscaping in its hardiness range and also for the cut flower industry.

Parentage: The new cultivar 'B-43-4' is a seedling selection resulting from the open pollination of *Ilex verticillata* 'OO15' (not patented), the seed parent, and an undesignated male *Ilex verticillata* plant, the pollen parent. In 2010, seeds were harvested from 'OO15' which resulted in approximately 144 seedlings. In March of 2011, the seedlings were transplanted into a field in Willow Creek, Calif. and grown to a mature size. From 2011 to 2013, these plants were evaluated for commercial production, based on criteria such as growth habit and fruiting habit. In August of 2013, one plant was observed which exhibited a tall, upright growth habit with a large number of strong main stems and a high density of very large salmon-orange berries along the entire length of the lateral branches. The new plant was isolated and grown to a mature size to confirm the distinctness and stability of the characteristics initially observed. After further evaluation and confirmation of the desirable traits, the claimed plant was finally selected for commercialization in August of 2014 and given the breeder denomination, 'B-43-4'.

Asexual Reproduction: In the fall of 2013, 'B-43-4' was first asexually reproduced in Willow Creek, Calif. by way of softwood stem cuttings taken from one year old growth. The claimed plant was found to asexually reproduce in uniform and stable manner and three successive cycles of vegetative propagation have proven to be true to type.

SUMMARY OF THE INVENTION

The following characteristics have been repeatedly observed and represent the distinguishing characteristics of the new *Ilex verticillata* cultivar 'B-43-4'. These traits, in combination, distinguish 'B-43-4' as a new and distinct cultivar.

1. 'B-43-4' exhibits a tall plant height; and
2. 'B-43-4' exhibits a large quantity of strong, upright main stems; and
3. 'B-43-4' exhibits short lateral branches; and
4. 'B-43-4' exhibits a large quantity of berries born along the entire length of the lateral branches, including the distal most portion of the lateral branches usually devoid of berries in the species which negates the need for manual pruning or use of plant growth regulators; and
5. 'B-43-4' exhibits very large salmon-orange berries which color slightly earlier in the growing season, approximating to the first of September in Willow Creek, Calif.

BOTANICAL DESCRIPTION OF THE PLANT

Figure 1:
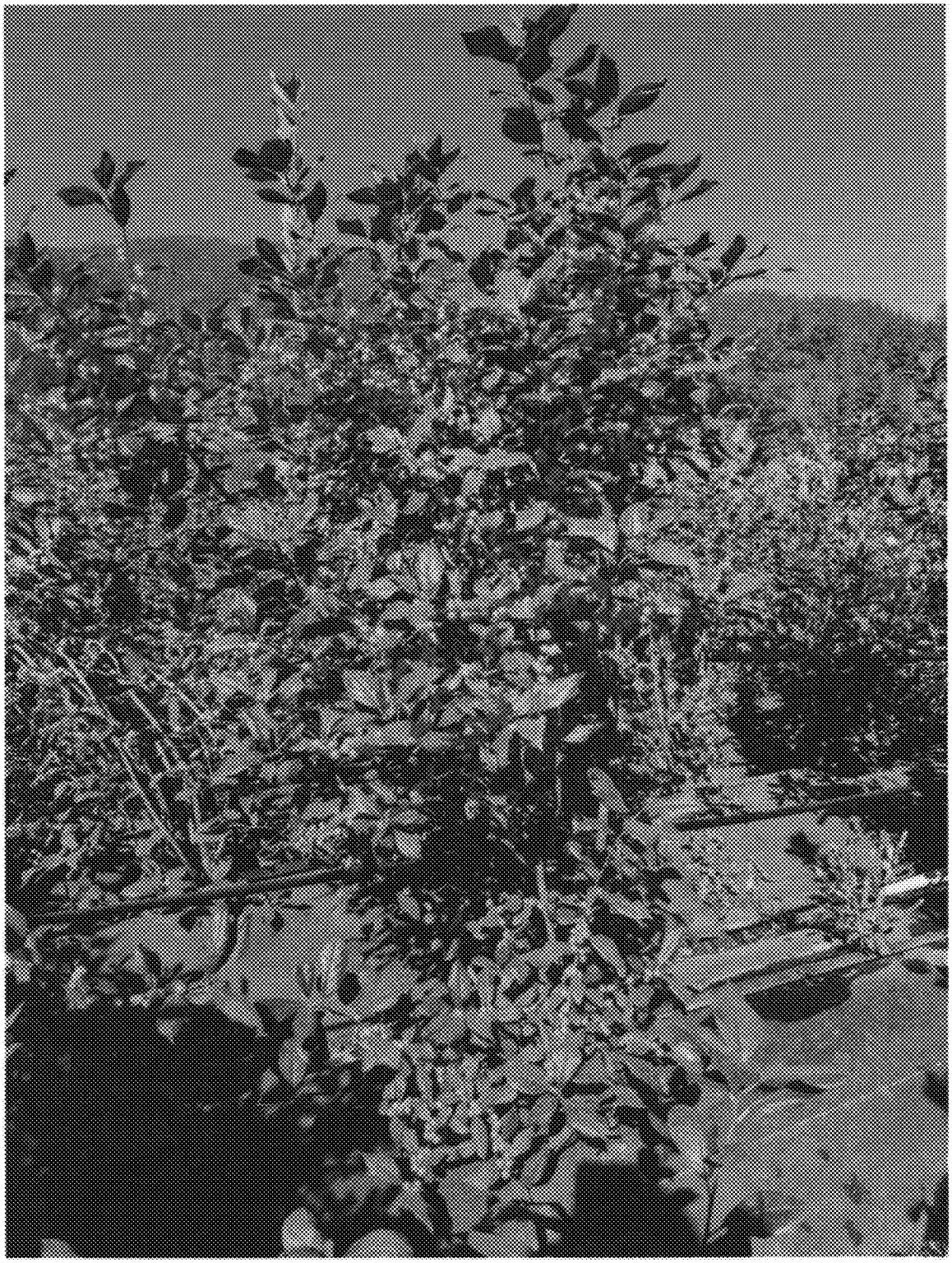
FIG. 1 illustrates, as nearly true as it is reasonably possible to make the same in color photographs of this type, an exemplary three and a half year old field-grown 'B-43-4' plant in Willow Creek, Calif.
Figure 2:
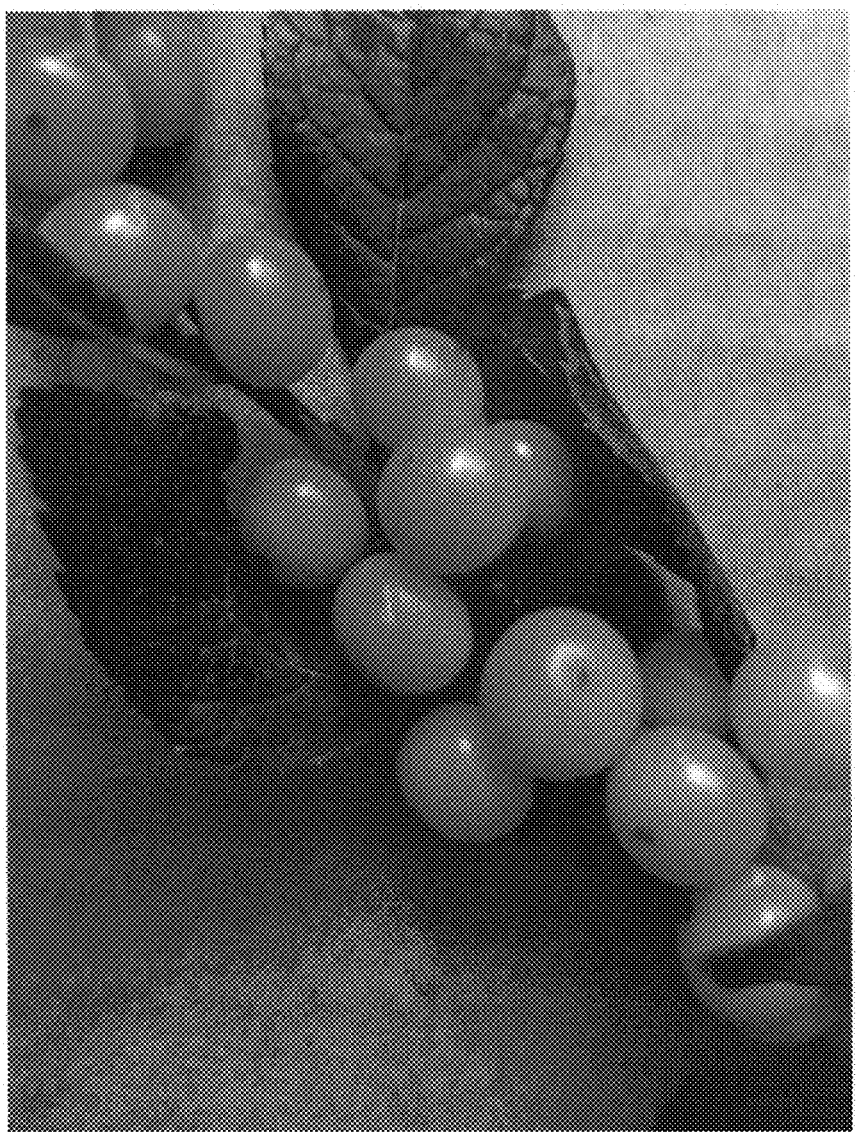
FIG. 2 illustrates, as nearly true as it is reasonably possible to make the same in color photographs of this type, a cut stem with fruit, harvested from an exemplary three and a half year old field grown 'B-43-4' plant in Willow Creek, Calif.

The following is a detailed botanical description of a new and distinct variety of a *Ilex verticillata* known as 'B-43-4'. Plant observations were made on field grown plants produced in Willow Creek, Calif. Unless indicated otherwise, the descriptions disclosed herein are based upon observations made of a mature 'B-43-4' plant, transplanted into a loamy clay field in May of 2016 as a one year old rooted cutting grown in a 4 inch nursery pot. The plant received morning shade and were grown using conventional production techniques for this species. The plant was provided overhead irrigation for two months after transplant and thereafter received regular drip irrigation. Fertilizer was regularly applied using a fertigation technique, and the plant was occasionally treated for mites when required. In the winter of 2016, the plant was pruned to 7 cm above soil level and have since been allowed to grow without further pruning. Observation data was recorded in the September of 2018.

Those skilled in the art will appreciate that certain characteristics will vary with older or, conversely, younger plants. 'B-43-4' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition except where common terms of color are used.

A botanical description of 'B-43-4' and comparisons with the known parent and closest known commercial comparator are provided below.

General plant description:

*Plant habit*.—Deciduous perennial shrub with an upright growth habit and excellent plant vigor. *Ilex verticillata* is a dioecious plant and 'B-43-4' is a female plant of the species.

*Height*.—Approximately 140 cm.

*Width*.—Approximately 80 cm.

*Environmental tolerances*.—Hardy in US Hardiness Zones 3 through 9; high tolerance to wind and rain.

*Pest and disease susceptibility or resistance*.—Plants have not been observed to be susceptible or resistant to pathogens and pests common to *Ilex verticillata*.

*Propagation*.—Propagation is accomplished using softwood stem cuttings.

*Time to develop roots*.—Approximately 21 days, in a propagation house with bottom heat and an average ambient temperature of 25 degrees Celsius.

*Crop time*.—Approximately 5 weeks are needed to produce a fully rooted cutting; after transplanting young plants grown in four inch nursery containers into a production field, fruit bearing stems can be harvested from the mature plants at the end of the second growing season.

Root system:

*Description*.—A network of larger primary roots and fine, fibrous lateral roots.

*Rooting habit*.—Freely branching, dense, and evenly distributed throughout the soil profile.

*Color, primary roots*.—Nearest to a mixture of greyed-yellow, RHS 161A, greyed-orange, RHS 165A, and greyed-brown, RHS 199A.

*Color, lateral roots*.—Nearest to a mixture of yellow-white, RHS 158A, orange-white, RHS 159B, and greyed-yellow, RHS 160C.

Stems:

*Branching habit*.—Free, basally branching habit; numerous upright main stems, each producing numerous lateral branches. Main stems are typically unbranched, yet occasionally branched. Main stems — Quantity — 16 observed. Attitude — Erect; near vertical. Cross section — Circular. Diameter — Up to 17 mm, at the base of the most mature stems. Length — Longest stem is 128 cm long. Internode length — Varying from 10 to 35 mm. Color — Yellow-green, nearest to RHS 148A, with densely reticulated fissures. The color of the fissures appears as a combination of greyed-green, RHS 197B, and greyed-brown, nearest to a mixture of RHS 199B, 199C and 199D. Texture — Glabrous and fissured; lenticels present. Lenticels are elliptical; approximately 1.0 mm long and 0. 5 mm wide; color is greyed-brown, RHS 199D. Strength — Very strong. Lateral branches — Quantity — Lower lateral branches senescing with age; 15 to 20 lateral branches per main stem which are mostly present on the upper half of main stems. Stem angle to main axis — In between 60 and 80 degrees. Cross-section — Circular. Diameter — 3 mm at the base. Length — An average of 7.5 cm. Internode length — Varying from 10 to 15 mm. Color, juvenile — Nearest to a combination of yellow-green, RHS 148A, and brown, RHS 200D. Color, mature — Nearest to a mixture of greyed-yellow and greyed. Texture — Smooth, glabrous; lenticels present. Lenticels are elliptical; approximately 1.0 mm long and 0.5 mm wide; color is greyed-brown, RHS 199D. Stem strength — Strong.

Foliage:

*Arrangement*.—Alternate.

*Attachment*.—Petiolate.

*Division*.—Simple.

*Shape*.—Elliptical.

*Length*.—68.5 mm on average.

*Width*.—33.4 mm on average.

*Apex*.—Acuminate.

*Base*.—Cuneate.

*Margin*.—Serrulate; slightly undulated.

*Aspect*.—Nearly flat.

*Texture and pubescence, adaxial surface*.—Glabrous and slightly rugose.

*Texture and pubescence, abaxial surface*.—Glabrous and slightly rugose.

*Color*.—Juvenile foliage, adaxial surface — Yellow-green, nearest to a mixture of RHS 151A, 152B and 152C. Juvenile foliage, abaxial surface — Yellow-green, RHS 146D. Mature foliage, adaxial surface — Dark yellow-green, nearest to RHS 147A. Mature foliage, abaxial surface — Yellow-green, RHS 147B.

*Venation*.—Pattern — Pinnate. Vein color, adaxial surface — The midrib is yellow-green, RHS 144B; all other veins are yellow-green, RHS 144A. Vein color, abaxial surface — Yellow-green, nearest to a mixture of RHS 145B and 145C.

*Petiole*.—Length — 10.5 mm. Diameter — 1.5 mm. Color, adaxial surface — Yellow-green, RHS 144B and suffused with greyed-orange, RHS 166A. Color, abaxial surface — Yellow-green, RHS 145C. Texture, adaxial and abaxial surfaces — Smooth; glabrous.

Inflorescence:

*Type*.—Solitary female flowers occurring at the leaf axils, with 1 to 3 flowers at each axil.

Flower bud:

*Shape*.—Globose to short ovoid.

*Dimensions*.—Ranging from 2.5 to 3.0 mm long and 2.5 mm in diameter.

*Color, upper and lower surfaces*.—Yellow-green, RHS 145D, at the base and becoming green-white towards the distal end, RHS 157A.

Flower:

*General description*.—Single rotate flowers with a shallow cup shape; flowers are female.

*Natural flowering season*.—May through early June in Willow Creek, Calif.

*Quantity*.—1 to 3 flowers per axil, with approximately 6 to 9 flowers on shorter proximal lateral branches and 27 to 33 on longer distal lateral branches.

*Lastingness*.—At greater than 25 degrees Celsius, petals drop away in approximately 5 days; at 15 degrees Celsius, petals drop away in approximately 8 days.

*Persistence*.—Not persistent.

*Fragrance*.—Not fragrant.

*Attitude*.—Flowers held upright and slightly outward.

*Dimensions*.—Corolla is 6.0 mm in diameter and 3.0 mm deep.

*Peduncle*.—Dimensions — 3.0 mm long and 0.75 mm in diameter. Color — Yellow-green, RHS 144C. Texture — Smooth; glabrous. Strength — Medium.

*Calyx*.—Shape — Sepals fused at the base forming a cup, with 6 to 7 rotate sepal lobes. Diameter — 2.0 to 2.5 mm, measured from apex of one sepal lobe to the apex of an opposing sepal lobe. Depth — 1.25 mm deep. Quantity of sepal lobes — 6 to 7 sepal lobes; typically 6. Apex, sepal lobes — Sepal lobes acute. Base — Fused. Margin — Entire; ciliate. Texture, inner and outer surfaces — Smooth and glabrous. Color when opening, inner surface — Yellow-green, a mixture of RHS 144D and 145C. Color when opening, outer surface — Yellow-green, a mixture of RHS 144D and 145C. Color when fully open, inner surface — Yellow-green, a mixture of RHS 144D and 145C. Color when fully open, outer surface — Yellow-green, a mixture of RHS 144D and 145C.

*Petals*.—Quantity of petals — 6 to 7 petals, fused at the base; typically with 7 petals. Arrangement — Single rotate whorl. Petal lobe apex — Obtuse. Petal lobe margin — Entire; slightly undulated. Texture, inner and outer surfaces — Smooth; glabrous. Luster, inner and outer surfaces — Matte to very slightly glossy. Color when opening, inner surface — White, RHS 155D. Color when opening, outer surface — White, RHS 155D. Color when fully open, dorsal surface — White, RHS 155D; petals are slightly translucent. Color when fully open, ventral surface — White, RHS 155D; petals are slightly translucent. Petal color fading to — Not fading.

Reproductive organs:

*Androecium*.—Stamens — Quantity — 6 to 7 sterile stamens. Position — Inserted; free. Attachment — One stamen attached at the base of each petal. Overall length — Approximately 1.0 mm long. Filament — Dimensions — 0.75 mm long and approximately 0.25 mm in diameter. Color — White, RHS 155D. Anthers — Attachment — Basifixed. Shape — Nearly globose, with a longitudinal split. Dimensions — 0.25 to 0.5 mm long and 0.5 mm wide. Color — White, RHS 155D. Pollen — None.

*Gynoecium*.—Pistils — Quantity — One; inferior to the corolla. Overall dimensions — Approximately 2.0 mm tall and 1.75 mm in diameter at the widest point. Stigma — Shape — Globular. Dimensions — 0.5 to 0.75 mm in diameter, and 0.5 mm to 0.75 mm tall. Color — Yellow-green, RHS 151D. Style — Shape — Relatively broad, and truncated. Dimensions — 0.75 to 1.0 mm tall and 0.75 to 1.0 mm in diameter. Color — Yellow-green, approximating to a mixture of RHS 144B and 151D. Ovary — Position — Superior. Dimensions — 0.75 to 1.0 mm tall and 0.75 to 1.0 mm in diameter. Color — Yellow-green, RHS 144C.

Fruit and seed:

*Fruit*.—Type — Simple, indehiscent berry. Time to maturity — Very early to fruit, maturing usually near the first week of September in Willow Creek, Calif. Shape — Globose. Quantity — 3 berries per axil, with approximately 6 to 9 berries on shorter proximal lateral branches and 27 to 33 on longer distal lateral branches. Dimensions — Approximately 10 mm in diameter, and 8 mm tall. Texture, pubescence and luster — Smooth, glabrous and glossy. Color, mature fruit — Orange, a mixture of RHS 25A, 26A and 26B.

*Seed*.—Quantity — Usually 4 per berry. Shape — Oblong, three-sided, with an ovate to deltoid outline. Dimensions — 3 mm long and 1.25 mm in diameter. Color — Greyed-orange, RHS 165D. Texture — Slightly rough.

COMPARISON WITH THE PARENT PLANTS

Plants of the new cultivar 'B-43-4' differ from the seed parent, *Ilex verticillata* 'OO15', by the characteristics described in Chart 1. The pollen parent is unknown and therefore no comparison is available.

CHART 1

| Characteristic | 'B-43-4' | 'OO15' |
|---|---|---|
| Timing of fruit maturation. | Typically in the first week of September; one week earlier than 'OO15'. | Typically in the second week of September; one week later than 'B-43-4'. |
| Productivity; number of harvestable cuttings per plant. | A single mature plant can yield up to 300 rooted cuttings. | A single mature plant can yields approximately 150 rooted cuttings. |
| Berry size. | Larger than those of 'OO15'. | Smaller than those of 'B-43-4'. |
| General coloration of the mature berry. | Salmon orange. | Red. |

COMPARISON WITH THE MOST SIMILAR *ILEX VERTICILLATA* CULTIVAR KNOWN TO THE INVENTOR

Plants of the new cultivar 'B-43-4' are most similar to the cultivar, *Ilex verticillata* 'Golden Verboom' (not patented). A comparison of 'B-43-4' with *Ilex* 'Golden Verboom' is described in Chart 2.

CHART 2

| Characteristic | 'B-43-4' | 'Golden Verboom' |
|---|---|---|
| Timing of fruit maturation. | Typically in the first week of September; three weeks earlier than 'Golden Verboom'. | Typically in the third week of September; approximately three weeks later than 'B-43-4'. |
| Occurrence of berries on lateral branches. | Berries present along the entire length of lateral branches, removing the need for manual pruning or plant growth regulator chemicals. | Berries only present on approximately 50 percent of lateral branches, requiring manual pruning or the use of a significant amount of plant growth regulator chemicals. |
| Productivity; number of harvestable main stems. | 25, resulting in more harvestable cut stems. | 12, resulting in much fewer harvestable cut stems. |
| General coloration of the mature berry. | Salmon orange. | Golden yellow. |

That which is claimed is:

1. A new and distinct variety of *Ilex verticillata* plant named 'B-43-4', substantially as described and illustrated herein.

* * * * *